United States Patent
Huebner et al.

(10) Patent No.: US 9,848,930 B2
(45) Date of Patent: Dec. 26, 2017

(54) STEERABLE FASTENER FOR BONE

(71) Applicants: Acumed LLC, Hillsboro, OR (US);
ACUTE Innovations LLC, Hillsboro, OR (US)

(72) Inventors: Randall J. Huebner, Portland, OR (US); Joel Gillard, Portland, OR (US)

(73) Assignees: Acumed LLC, Hillsboro, OR (US); Acute Innovations LLC, Hillsboro, OR (US)

(*) Notice: Subject to any disclaimer, the term of this patent is extended or adjusted under 35 U.S.C. 154(b) by 759 days.

(21) Appl. No.: 14/322,796

(22) Filed: Jul. 2, 2014

(65) Prior Publication Data

US 2015/0012048 A1    Jan. 8, 2015

Related U.S. Application Data

(60) Provisional application No. 61/842,776, filed on Jul. 3, 2013.

(51) Int. Cl.
*A61B 17/04* (2006.01)
*A61B 17/86* (2006.01)
(Continued)

(52) U.S. Cl.
CPC .......... *A61B 17/864* (2013.01); *A61B 17/68* (2013.01); *A61B 17/863* (2013.01);
(Continued)

(58) Field of Classification Search
None
See application file for complete search history.

(56) References Cited

U.S. PATENT DOCUMENTS

| 5,002,543 A | 3/1991 | Bradshaw et al. |
| 6,648,890 B2 | 11/2003 | Culbert et al. |

(Continued)

FOREIGN PATENT DOCUMENTS

| EP | 1273269 A2 | 1/2003 |
| EP | 1728480 A1 | 6/2006 |

(Continued)

OTHER PUBLICATIONS

Fourcade, Olivier, Examiner, European Patent Office, "Extended European Search Report" in connection with related European Patent Application No. 14820661.8, dated Jan. 23, 2017, 7 pages.

(Continued)

*Primary Examiner* — Sameh Boles
(74) *Attorney, Agent, or Firm* — Kolisch Hartwell, P.C.

(57) ABSTRACT

Bone fixation system including methods, apparatus, and kits, for steering a leading end of a fastener within bone. In some embodiments, the system may include (a) a flexible fastener having an external thread, and (b) a guide including a graspable handle attached or attachable to a wire having a distal end portion with a preformed longitudinal curvature in a direction indicated by the handle. The wire may be extendable through the fastener and configured to be advanced longitudinally, while extending through the fastener, such that the distal end portion of the wire penetrates bone ahead of a leading end of the fastener and creates a curved travel path for the leading end of the fastener.

20 Claims, 14 Drawing Sheets

(51) Int. Cl.
*A61F 2/08* (2006.01)
*A61B 17/68* (2006.01)
*A61B 17/88* (2006.01)

(52) U.S. Cl.
CPC ........ *A61B 17/869* (2013.01); *A61B 17/8685* (2013.01); *A61B 17/8897* (2013.01); *A61B 17/8875* (2013.01); *A61B 2017/681* (2013.01)

(56) References Cited

U.S. PATENT DOCUMENTS

| | | |
|---|---|---|
| 7,625,395 B2 | 12/2009 | Mückter |
| 8,287,539 B2 | 10/2012 | Nelson et al. |
| 8,287,541 B2 | 10/2012 | Nelson et al. |
| 8,317,846 B2 | 11/2012 | Bottlang |
| 8,343,197 B2 | 1/2013 | Gonzalez-Hernandez |
| 8,366,559 B2 | 2/2013 | Papenfuss et al. |
| 8,439,917 B2 | 5/2013 | Saravia et al. |
| 2006/0129153 A1 | 6/2006 | Klaue et al. |
| 2009/0149890 A1 | 6/2009 | Martin |
| 2009/0210016 A1 | 8/2009 | Champagne |
| 2010/0292695 A1 | 11/2010 | May et al. |
| 2011/0144645 A1* | 6/2011 | Saravia ............ A61B 17/1725 606/63 |
| 2011/0144703 A1 | 6/2011 | Krause et al. |
| 2011/0160772 A1 | 6/2011 | Arcenio et al. |
| 2011/0282397 A1 | 11/2011 | Richter et al. |
| 2012/0232597 A1 | 9/2012 | Saidha et al. |
| 2013/0131678 A1 | 5/2013 | Dahners |

FOREIGN PATENT DOCUMENTS

| | | |
|---|---|---|
| EP | 2140823 A1 | 1/2010 |
| WO | 9522290 A1 | 8/1995 |
| WO | 2009076086 A1 | 6/2009 |
| WO | 2010099239 A2 | 9/2010 |

OTHER PUBLICATIONS

Shane Thomas, Authorized Officer, Commissioner for Patents, "International Search Report" in connection with related PCT Patent Application No. PCT/US2014/045314, dated Nov. 24, 2014, 2 pages.

Shane Thomas, Authorized Officer, Commissioner for Patents, "Written Opinion of the International Searching Authority" in connection with related PCT Patent Application No. PCT/US2014/045314, dated Nov. 24, 2014, 6 pages.

* cited by examiner

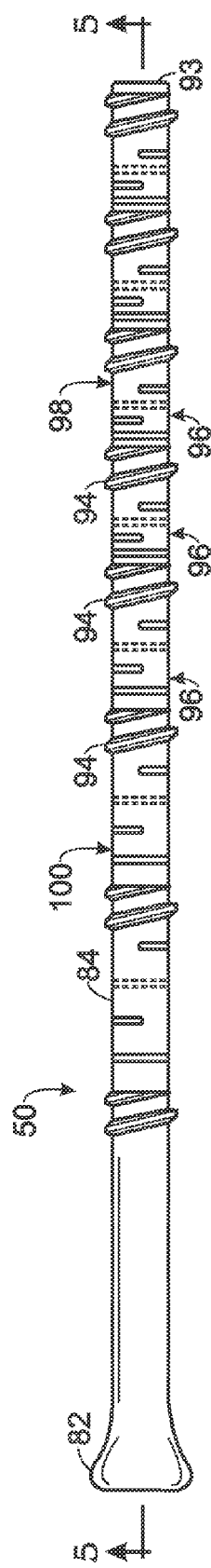
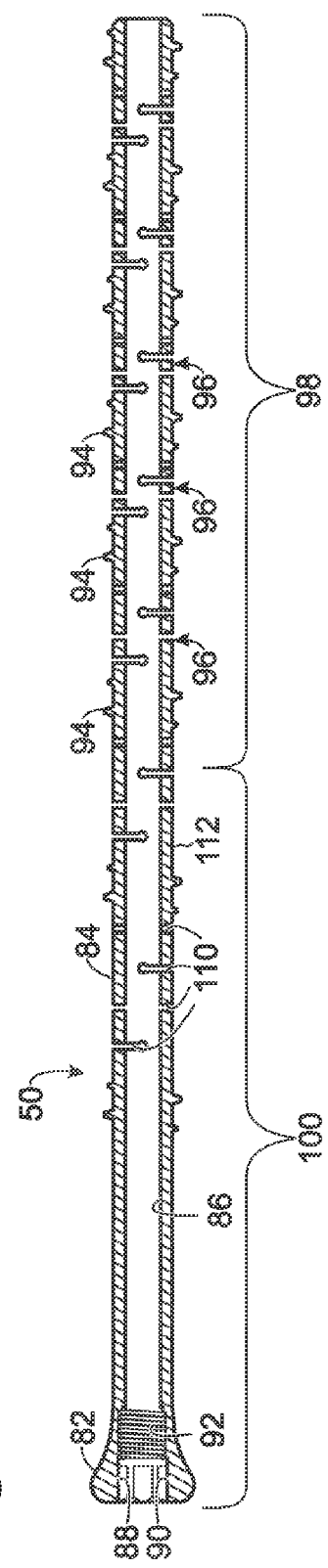
Fig. 4
Fig. 5

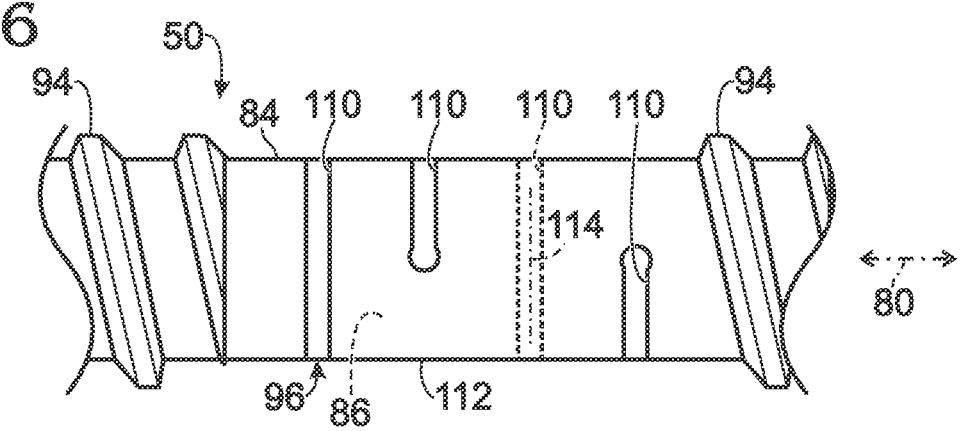
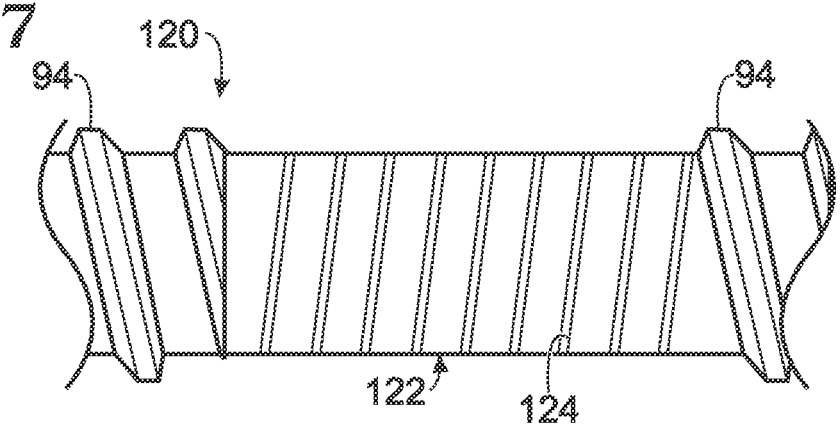
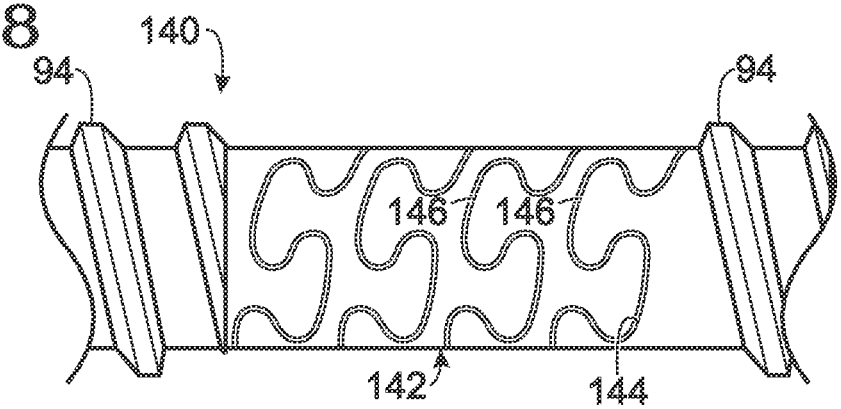

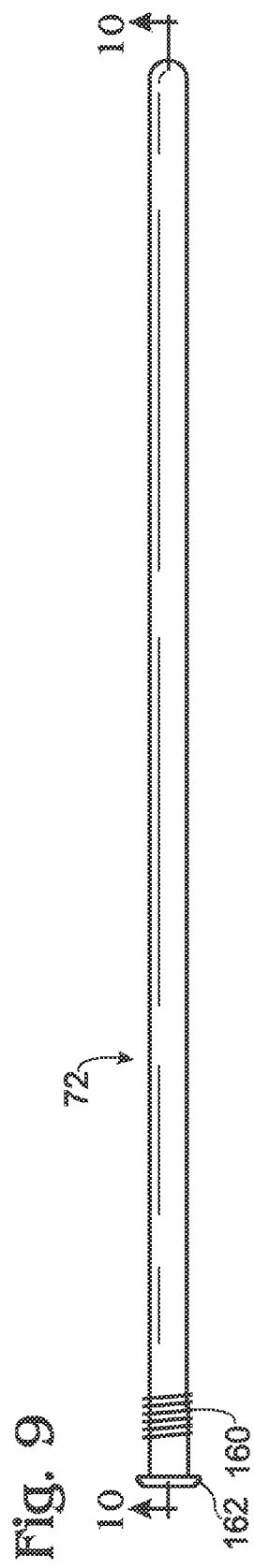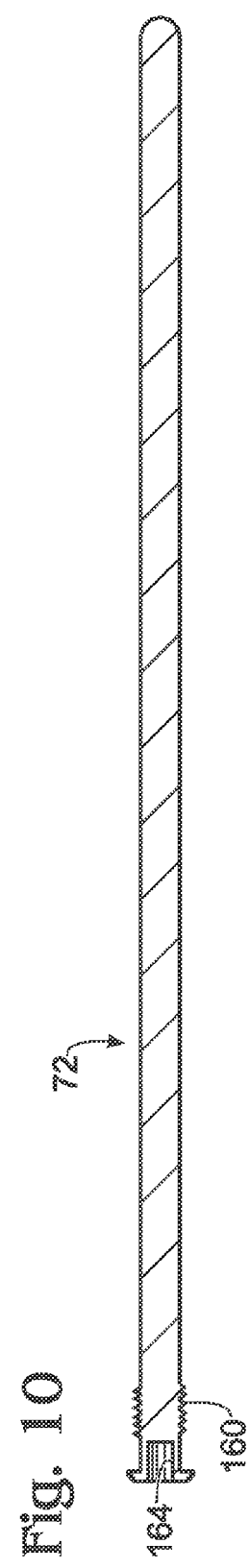

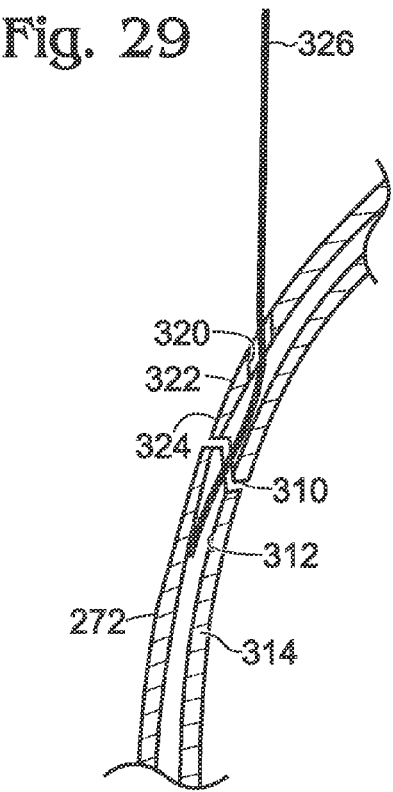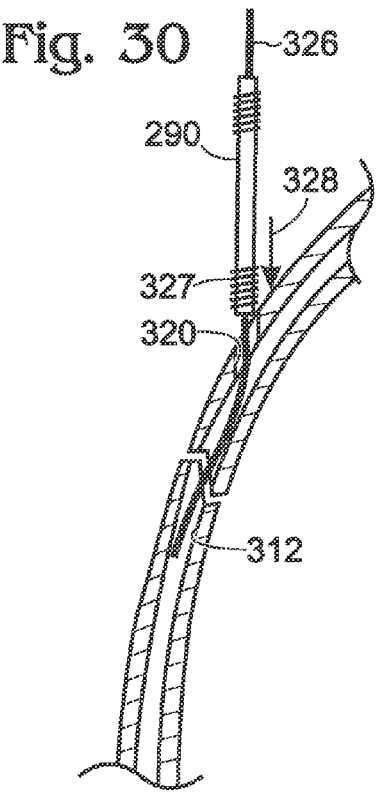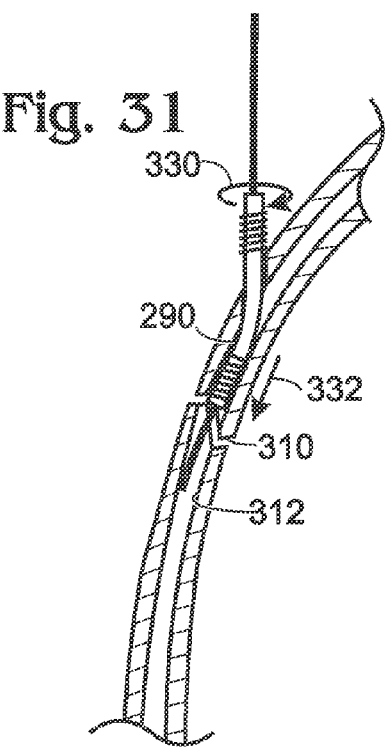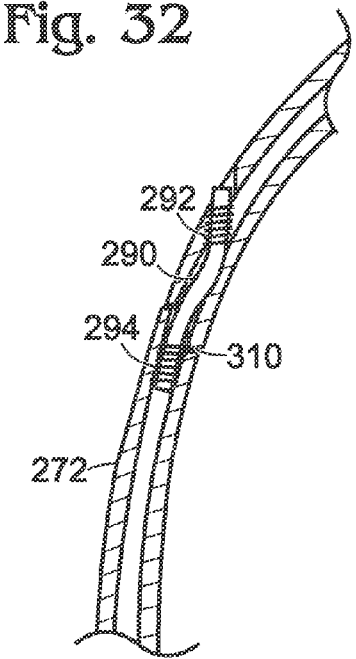

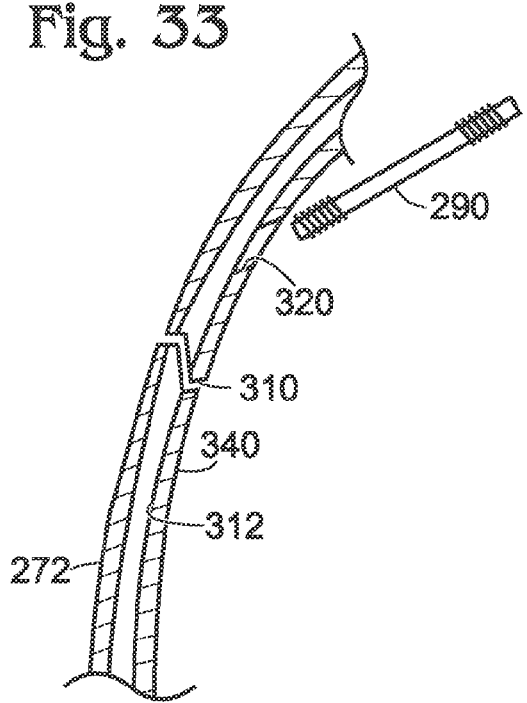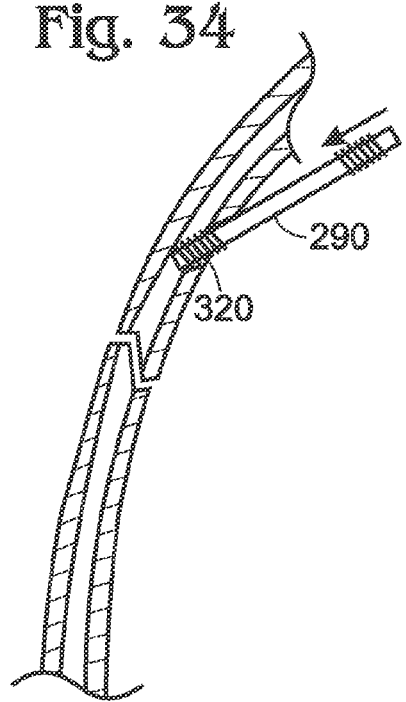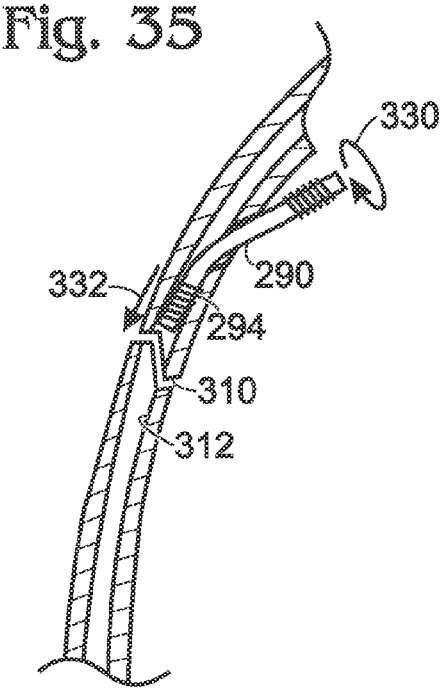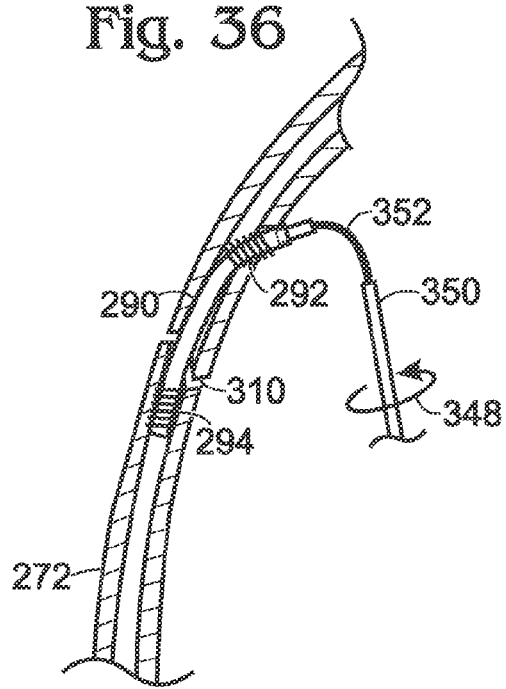

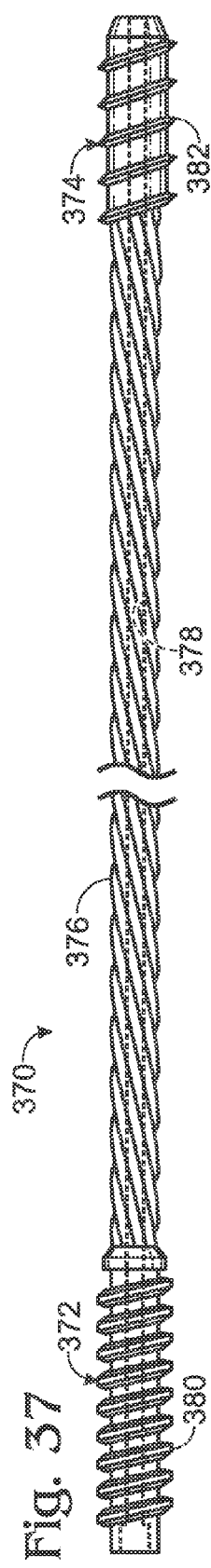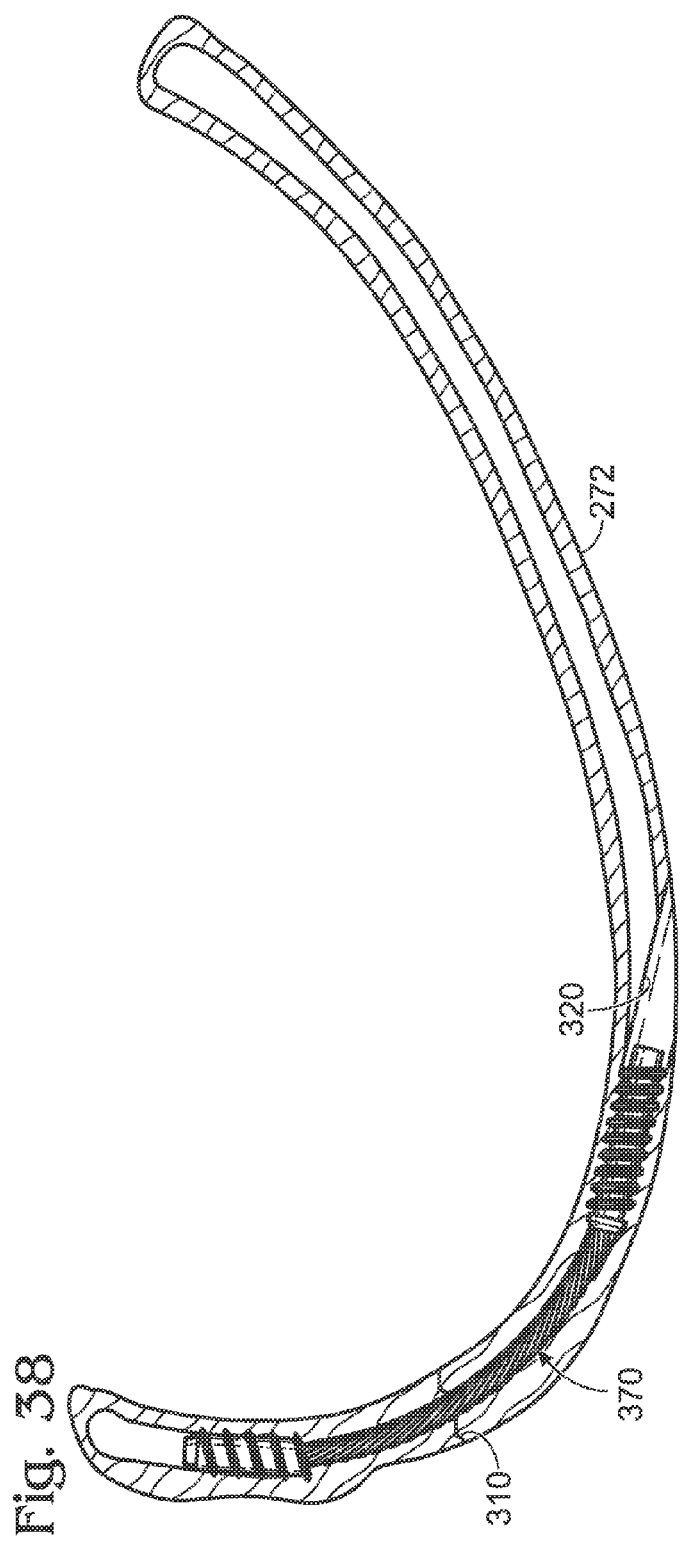

STEERABLE FASTENER FOR BONE

CROSS-REFERENCE TO PRIORITY APPLICATION

This application is based upon and claims the benefit under 35 U.S.C. §119(e) of U.S. Provisional Patent Application Ser. No. 61/842,776, filed Jul. 3, 2013, which is incorporated herein by reference in its entirety for all purposes.

INTRODUCTION

The human skeleton is composed of 206 individual bones that perform a variety of important functions, including support, movement, protection, storage of minerals, and formation of blood cells. These bones can be grouped into two categories, the axial skeleton and the appendicular skeleton. The axial skeleton consists of 80 bones that make up the body's center of gravity, and the appendicular skeleton consists of 126 bones that make up the body's appendages. The axial skeleton includes the skull, vertebral column, ribs, and sternum, among others, and the appendicular skeleton includes the long bones of the upper and lower limbs, and the clavicles and other bones that attach these long bones to the axial skeleton, among others.

To ensure that the skeleton retains its ability to perform its important functions, and to reduce pain and disfigurement, fractured bones should be repaired promptly and properly. Typically, fractured bones are treated using a fixation device that reinforces the bone and keeps bone segments aligned during healing. Fixation devices may take a variety of forms, including casts for external fixation and screws for internal fixation. To use a screw to repair a fractured bone, a surgeon (1) selects an appropriate screw, (2) reduces (sets) the fracture, and (3) places the screw into the bone with the screw crossing the fracture, so that fragments of the bone are fixed relative to one another.

Bone screws generally are placed into bone on a predefined trajectory. For example, a drill may be used to form a hole in bone before screw placement. The screw follows the hole as the screw is driven into the bone. Alternatively, the screw, if cannulated, may follow a trajectory defined by a pre-installed wire. The screw is placed onto the wire, with the wire extending through the screw, and then the wire guides advancement of the bone screw, coaxial to the wire, as the screw is turned. In either case, it is not feasible for the surgeon to modify the trajectory of the bone screw after the leading end has entered bone.

SUMMARY

The present disclosure provides a bone fixation system including methods, apparatus, and kits, for steering a leading end of a fastener within bone. In some embodiments, the system may include (a) a flexible fastener having an external thread, and (b) a guide including a graspable handle attached or attachable to a wire having a distal end portion with a preformed longitudinal curvature in a direction indicated by the handle. The wire may be extendable through the fastener and configured to be advanced longitudinally, while extending through the fastener, such that the distal end portion of the wire penetrates bone ahead of a leading end of the fastener and creates a curved travel path for the leading end of the fastener.

BRIEF DESCRIPTION OF THE DRAWINGS

FIG. 4 is a side view of the fastener of FIG. 2 taken in the absence of other system components.

FIG. 5 is a sectional view of the fastener of FIG. 2 taken generally along line 5-5 of FIG. 4.

FIG. 6 is a fragmentary view of a flexible region of the shaft of the fastener of FIG. 2, taken generally between a pair of threads formed on the shaft and illustrating discrete slots that impart flexibility to the shaft.

FIG. 7 is a fragmentary view of another exemplary flexible region that may be included in the shaft of the fastener of FIG. 2, taken generally as in FIG. 6 but with discrete slots replaced by a single helical slot, in accordance with aspects of the present disclosure.

FIG. 8 is a fragmentary view of still another exemplary flexible region that may be included in the shaft of the fastener of FIG. 2, taken generally as in FIG. 6 but with the discrete slots replaced by a generally helical, serpentine slot forming interlocking dovetails, in accordance with aspects of the present disclosure.

FIG. 9 is a side view of the stiffener of FIG. 2 taken in isolation from other system components.

FIG. 10 is a sectional view of the stiffener of FIG. 9, taken generally along line 10-10 of FIG. 9.

FIGS. 29-32 are a series of partially sectional configurations produced with the flexible fastener of FIG. 27 and a fractured rib during performance an exemplary method of fixing the fractured rib, with the fastener placed into the rib from an outer side thereof, and with the path of the fastener determined by a guide, in accordance with aspects of the present disclosure.

FIGS. 33-36 are a series of configurations produced with the flexible fastener of FIG. 27 and the fractured rib of FIG. 29 during performance an exemplary method of fixing the fractured rib, with the fastener placed into the rib from an inner side thereof, and with the path the fastener determined by a guide, in accordance with aspects of the present disclosure.

FIG. 37 is a side view of another exemplary flexible fastener for fixation of a bone, such as a rib bone, in accordance with aspects of the present disclosure.

FIG. 38 is a sectional view of a fractured rib bone fixed with the flexible fastener of FIG. 37, in accordance with aspects of the present disclosure.

DETAILED DESCRIPTION

The present disclosure provides a bone fixation system including methods, apparatus, and kits, for steering a leading end of a fastener within bone. In some embodiments, the system may include (a) a flexible fastener having an external thread, and (b) a guide including a graspable handle attached or attachable to a wire having a distal end portion with a preformed longitudinal curvature in a direction indicated by the handle. The wire may be extendable through the fastener and configured to be advanced longitudinally, while extending through the fastener, such that the distal end portion of the wire penetrates bone ahead of a leading end of the fastener and creates a curved travel path for the leading end of the fastener.

Further aspects of the present disclosure are described in the following sections: (I) bone fixation system with a flexible fastener, (II) methods of installing a flexible fastener, (III) rib fixation with a flexible fastener, (IV) composition of system components, and (V) systems/kits.

I. Bone Fixation System with a Flexible Fastener

This section describes an exemplary system for bone fixation with a flexible fastener; see FIGS. 1-15.

Figure 1:
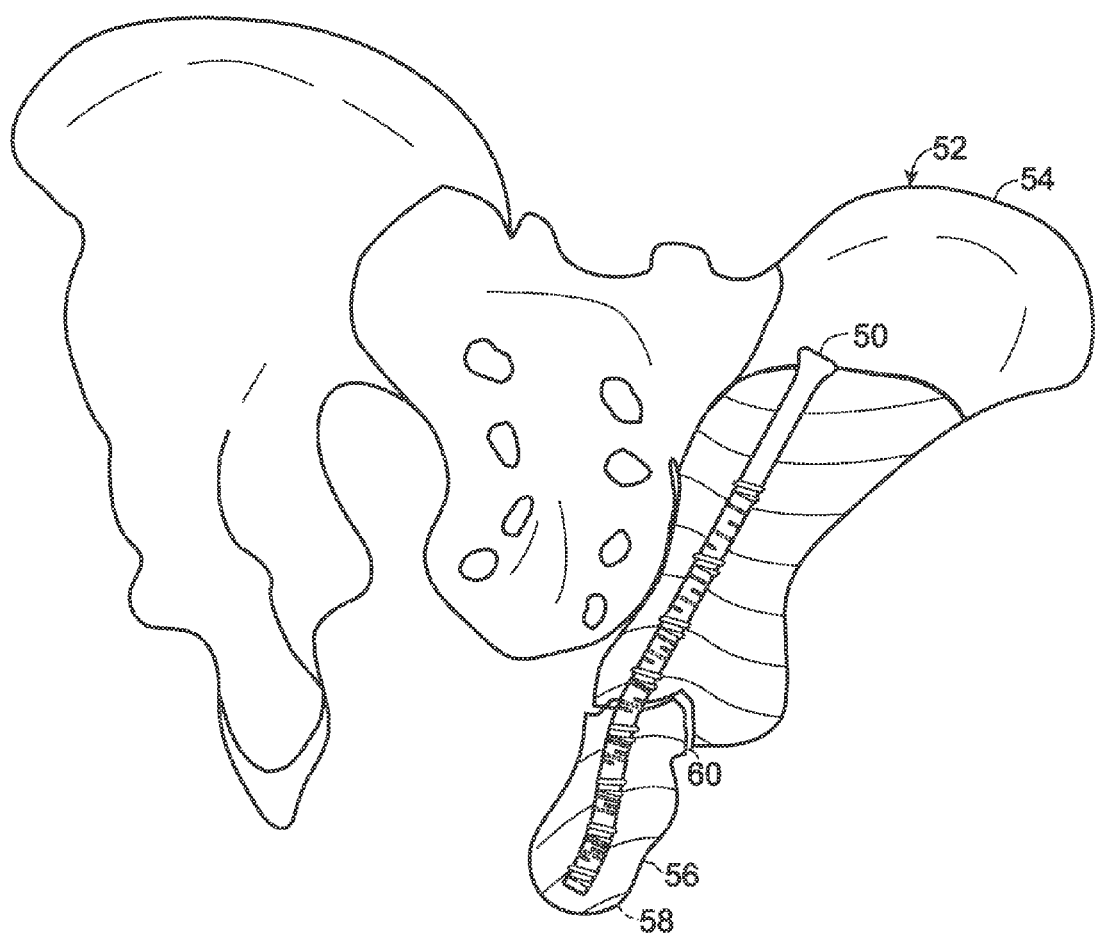
FIG. 1 is a sectional view of a fractured pelvis fixed with an exemplary steerable fastener, in accordance with aspects of the present disclosure.

FIG. 1 shows an exemplary flexible fastener 50 installed in and fixing a fractured pelvis 52. (Fastener 50 interchangeably may be termed an implant, a fixation device, a flexible fastener, a screw, or a bone screw.) Fastener 50 may be placed into a hip bone of pelvis 52 from a superior position (i.e., a position toward the head of a patient from the pelvis) such as an upper border of illium 54, and may extend down a pelvic column to ischium 56 or pubis 58, among others. The fastener may span one or more discontinuities, such as at least one fracture 60. The fastener may follow a nonlinear path, as shown, according to bone shape and fragment position, which may allow the fastener to reach each bone fragment, even if the bone fragment is somewhat displaced, the bone has a curvilinear shape, or an obstacle (e.g., another implant) needs to be circumnavigated.

Figure 2:
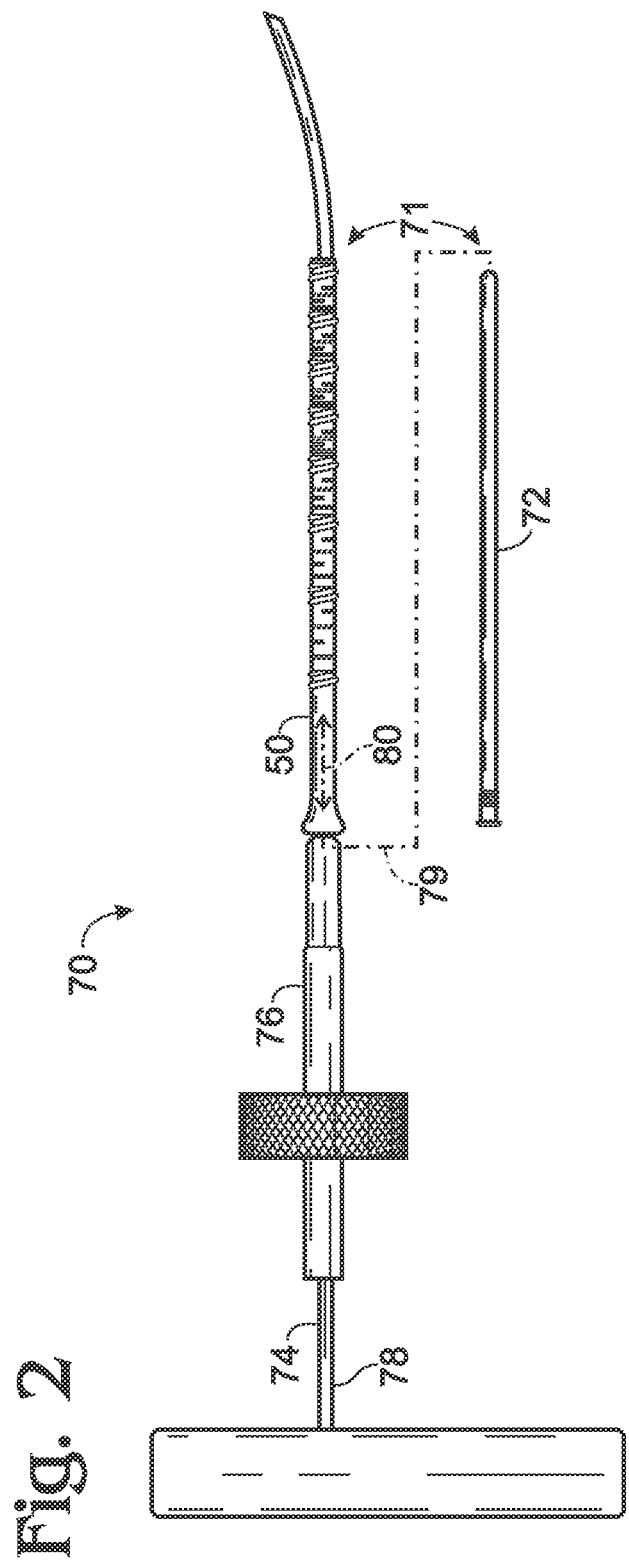
FIG. 2 is a side, partially exploded view of selected aspects of an exemplary bone fixation system including the steerable fastener of FIG. 1, with the fastener disposed as a sleeve on a wire of a guide, mated with a driver, and disposed above an insertable stiffener, in accordance with aspects of the present disclosure.

FIG. 2 shows an exemplary bone fixation system 70 including a fixation assembly 71 that may be formed by fastener 50 and an insertable stiffener 72 (interchangeably termed an "elongate insert" or a "reinforcing insert"). The fastener may be structured to receive stiffener 72 after the fastener has been placed at least substantially completely into bone. The system also may include instruments for installation of the fastener, such as a guide 74 and a driver 76. Guide 74 may include a wire 78 that is extendable longitudinally through both driver 76 and fastener 50, allowing the wire to penetrate bone ahead of the fastener. The guide creates a track along which the fastener can be advanced within bone. Driver 76 may be operatively mated with fastener 50, as shown, so that rotation of the driver about the wire drives the fastener over the track created by the wire within bone.

Figure 3:
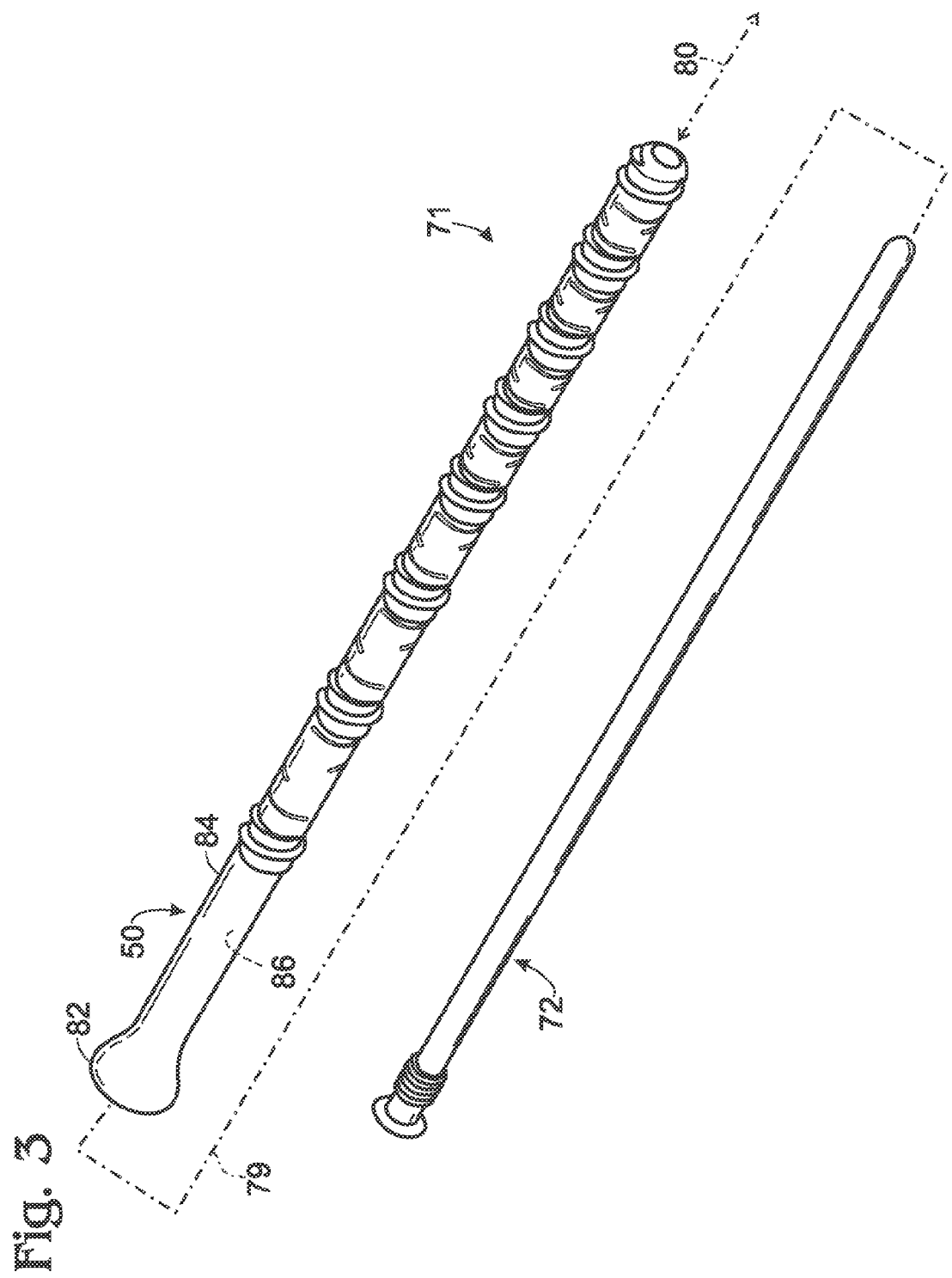
FIG. 3 is an exploded isometric view of the fastener and stiffener of FIG. 2.

FIG. 3 shows fastener 50 and reinforcing stiffener 72 in the absence of the installation instruments of the system. Stiffener 72 may be sized and shaped to be received in and attached to fastener 50, indicated at 79, with the stiffener arranged coaxially to a longitudinal axis 80 defined by fastener 50.

FIGS. 3-5 show further aspects of fastener 50. The fastener may have a head 82, and a shaft 84 arranged adjacent the head. Fastener 50 may be cannulated, defining an axial channel 86 (interchangeably termed a longitudinal through-hole) that extends longitudinally through the fastener between opposing ends thereof.

Head 82 may have a greater average diameter than the shaft and may define an internal and/or external contact region 88 for the driver (see FIG. 5). For example, in the depicted embodiment, the head defines a hexagonal recess 90 to receive the distal end of the driver. Head 82 may taper and/or narrow stepwise toward shaft 84. The head and/or the shaft may define an attachment structure, such as an internal thread 92, for engagement with stiffener 72.

Shaft 84 may be continuous with head 82. Accordingly, the head and the shaft may be connected integrally, and collectively may be only one piece. The shaft may be cylindrical or conical, among others, and may (or may not) taper toward a leading end 93 of the fastener to facilitate placement into and advancement in bone. The fastener may be self-drilling; leading end 93 may define one or more teeth to cut bone as the fastener is advanced rotationally in bone.

Shaft 84 (and/or head 82) may have at least one external thread formed thereon. For example, in the depicted embodiment, fastener 50 has a plurality of discrete, spaced thread segments 94 (interchangeably termed threads) (see FIGS. 4 and 5). Threads 94 all may follow the same helical path and may have the same pitch as one another or may have distinct pitches (e.g., with a smaller pitch toward the proximal/trailing end of the fastener). The threads may be uniformly or non-uniformly distributed along the shaft. In other embodiments, shaft 84 may have a single, substantially continuous thread formed thereon, or a proximal thread and a distal thread separated by a non-threaded region of the shaft. In any event, one or more threads 94 may extend collectively along any suitable portion of the length of the shaft, such as less than one-half or greater than one-half of the length of the shaft.

Shaft 84 (and/or fastener 50) may be flexible, which means that the shaft (and/or fastener 50) may be deformed from a linear configuration to a nonlinear configuration during installation of the fastener. The flexibility of the shaft may be uniform along at least a majority of the length of the shaft or may be localized to a single region or a plurality of spaced regions. The depicted embodiment has a plurality of flexible regions 96 arranged along the shaft from one another and separated by threads 94. The flexible regions may be distributed uniformly or non-uniformly along the shaft. For example, in the depicted embodiment, flexible regions 96 are more numerous in a distal half 98 of the fastener and are closer to one another in the distal half relative to a proximal half 100 of the fastener. Accordingly, the fastener may be more flexible distally (e.g., in distal half 98) than proximally (e.g., in proximal half 100).

FIG. 6 shows a fragmentary view of fastener 50 taken at one of flexible regions 96 between an adjacent pair of threads 94. The shaft of the fastener may define a plurality of discrete slots 110 that impart flexibility to the shaft. Each slot 110 may cut through a circumferential wall 112 of shaft 84, to provide communication between the exterior and channel 86 of the shaft (also see FIG. 5). The slot may (or may not) be planar, extending in a plane 114 between opposing ends of the slot. Each slot may be arranged transversely (e.g., orthogonally) to longitudinal axis 80 of the fastener. The slots may be rotationally offset from one another about longitudinal axis 80. For example, in the depicted embodiment, each flexible region 96 has four slots 110 that each are offset from adjacent slots by about 90 degrees. In other examples, the flexible region may have fewer or more slots (e.g., three slots offset from one another by about 120 degrees, six slots each offset from adjacent slots by about 60 degrees, and so on). In some cases, slots 110 may overlap a threaded region of the shaft, to render the threaded region flexible.

FIG. 7 shows a fragmentary view of another exemplary flexible fastener 120 that may be utilized in system 70 in place of fastener 50 (also see FIG. 2). Fastener 120 may have any suitable combination of the features disclosed above for fastener 50. A flexible region 122 of the fastener's shaft may include a helical slot 124 that cuts through the circumferential wall of the shaft and extends about the longitudinal axis multiple times. Slot 124 may or may not overlap a thread of the fastener.

FIG. 8 shows a fragmentary view of yet another exemplary flexible fastener 140 that may be utilized in system 70 in place of fastener 50 (also see FIG. 2). Fastener 140 may have any suitable combination of the features disclosed above for fastener 50. A flexible region 142 of the fastener's shaft may include a serpentine, generally helical slot 144 that cuts through the circumferential wall of the shaft and extends about the longitudinal axis multiple times. Slot 144 may or may not overlap a thread of the fastener. The serpentine structure of the slot may form a plurality of dovetail joints 146 that restrict torsional deformation of the shaft, while permitting shaft flexion and torque transmission.

FIGS. 9 and 10 show reinforcing stiffener 72. The stiffener may be sufficiently flexible to conform to the longitudinal shape of fastener 50 when the fastener is held in a nonlinear configuration by bone. The stiffener may be cylindrical and may be sized to be received in axial channel 86 of the fastener (also see FIG. 5). The length of the stiffener may correspond to the length of fastener 50, such as being more than half as long as the fastener. In the present illustration, the stiffener may be about the same length as the fastener, for example, slightly shorter (or slightly longer).

Stiffener 72 may be attachable to fastener 50, such as by threaded engagement. For example, the stiffener may define an external thread 160 that is complementary to internal thread 92 of fastener 50 (also see FIG. 5). A head 162 of the stiffener may act as a stop during stiffener installation in fastener 50 and may at least partially define a driver engagement structure 164.

Figure 11:
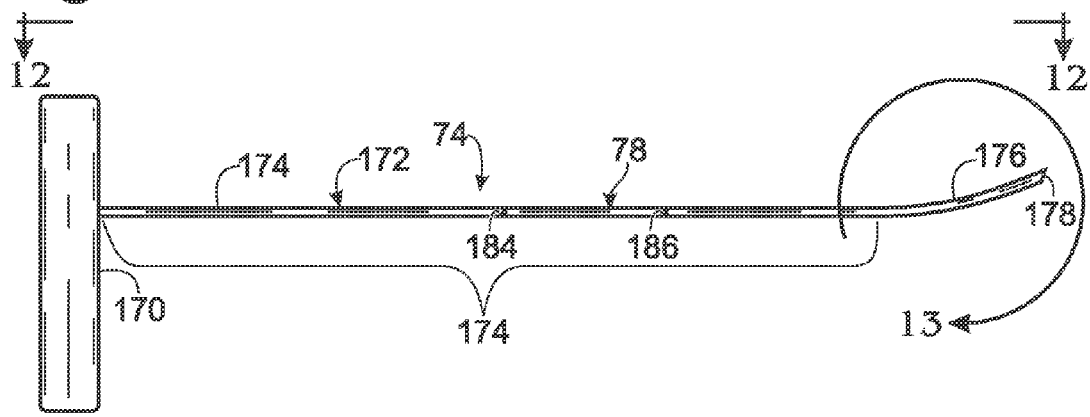
FIG. 11 is a side view of the guide of the system of FIG. 2 taken in isolation from other system components.
Figure 12:
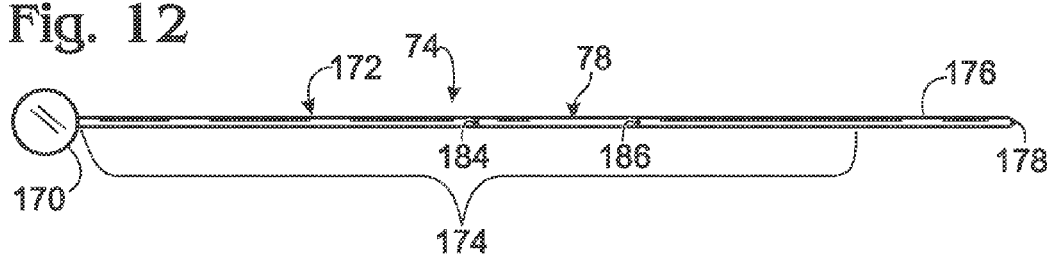
FIG. 12 is top view of the guide of FIG. 11, taken generally along line 12-12 of FIG. 11.
Figure 13:
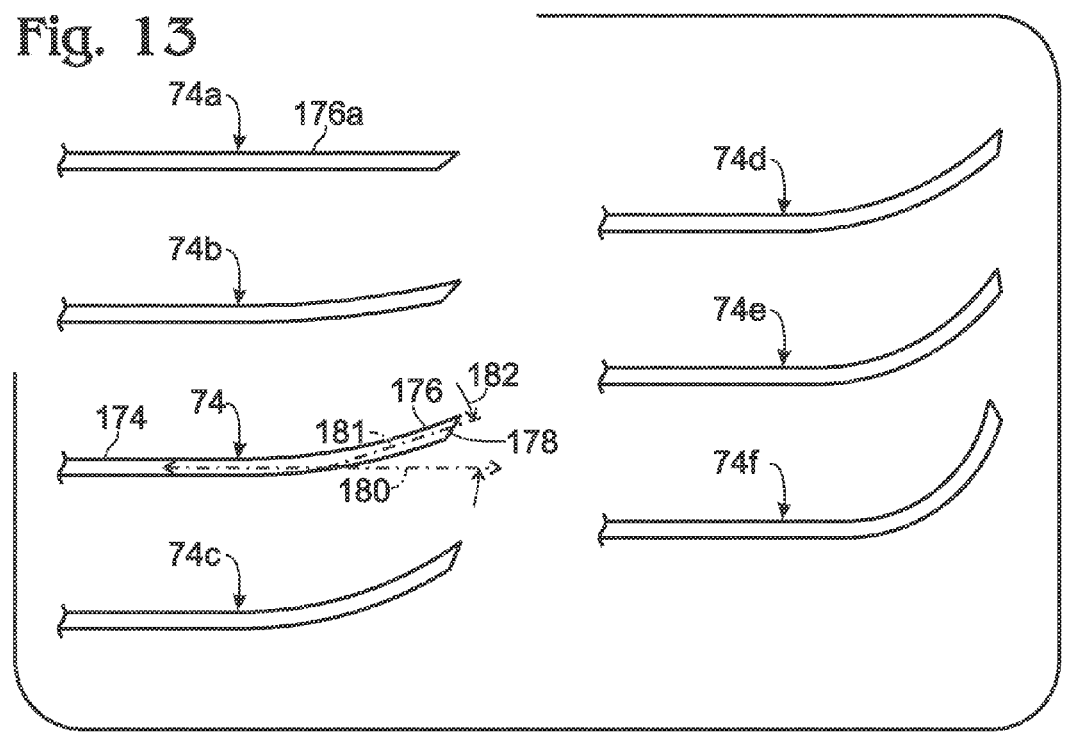
FIG. 13 is a fragmentary view of a set of exemplary guides that may be included in the system of FIG. 2, taken around a distal end portion of each guide, as indicated generally at "13" in FIG. 11, and illustrating different shapes, such as distinct radii of curvature, that may be present in the distal end portions of the guides.

FIGS. 11-13 show views of guide 74. The guide may include a graspable handle 170 and wire 78 attached to the handle. The wire may be arranged transversely (e.g., orthogonally) to the handle and may be coplanar with the handle. Also, the wire may be offset from a central transverse plane of the handle. Accordingly, the orientation of the wire and particularly its direction of curvature (e.g., within bone) may be indicated to the user by the orientation of the handle. More generally, be shaped, positioned, and/or marked to indicate the direction in which the wire curves.

Wire 78 may have any suitable properties. The wire may be sufficiently flexible to conform to a nonlinear shape assumed by fastener 50 disposed in bone. The wire may have a diameter that is less than axial channel 86 of fastener 50 (also see FIG. 5), to allow the wire to extend through the fastener (and driver 76; see FIG. 2). The wire may (or may not) have a circular cross section and may (or may not) be cylindrical.

The wire may have any suitable shape. The wire may have a proximal portion 174 and a distal end portion 176. The proximal portion may (or may not) extend linearly in a direction away from the handle to the distal end portion. The distal end portion may extend nonlinearly or linearly (e.g., coaxially) from proximal portion 174 to a tip 178, which may be pointed. In the depicted embodiment, distal end portion 176 is curved, such that tip 178 is offset from a long axis 180 defined by proximal portion 174 (see guide 74 in FIG. 13). A line 181 extending from tip 178 to the junction between proximal portion 174 and distal end portion 176 may define any suitable angle 182 with long axis 180, such as about zero degrees, or at least about 5, 10, or 15 degrees, among others.

The wire may include one or more reference marks (also termed depth indicators), such as marks 184 and 186, that indicate the position of tip 178 and/or distal end portion 176 with respect to fastener 50 and/or bone. For example, in the depicted embodiment, mark 184 is configured to be visibly located adjacent the proximal boundary of fastener 50 when all of distal end portion 176 (and none of proximal portion 174) projects from the leading end of fastener 50. Also, mark 186 is configured to be visibly located adjacent the proximal boundary of fastener 50 when approximately none of distal end portion 176 projects from the leading end of the fastener (i.e., when tip 178 is even with the leading boundary of fastener 50).

Tip 178 may be formed by a tapered end of wire 78. The end may have one or more beveled surface regions and/or may be pointed. In some cases, the end may have a plurality of beveled surface regions that are angularly offset from one another around the local long axis of the guide to form a pointed tip. For example, the tip may have three beveled surface regions that are offset from one another by about 120 degrees, four beveled surface regions that are offset from one another by about 90 degrees, or the like.

FIG. 13 shows the distal end portions of the wires of a set of exemplary guides 74 and 74a-74f that may be included in the system of FIG. 2, each taken generally at the region identified at "13" in FIG. 11. The distal end portions may differ from one another by radius of curvature, the size of angle 182 defined by the distal end portion and a linear portion of wire, the length of the distal end portion, or the like. For example, the set of guides may provide angles 182 covering a range of any suitable magnitude, such as at least about 5, 10, or 20 degrees, among others. Any combination of the guides may be used interchangeably in any suitable order during installation of a flexible fastener, to steer the leading end of the fastener in bone.

Figure 14:
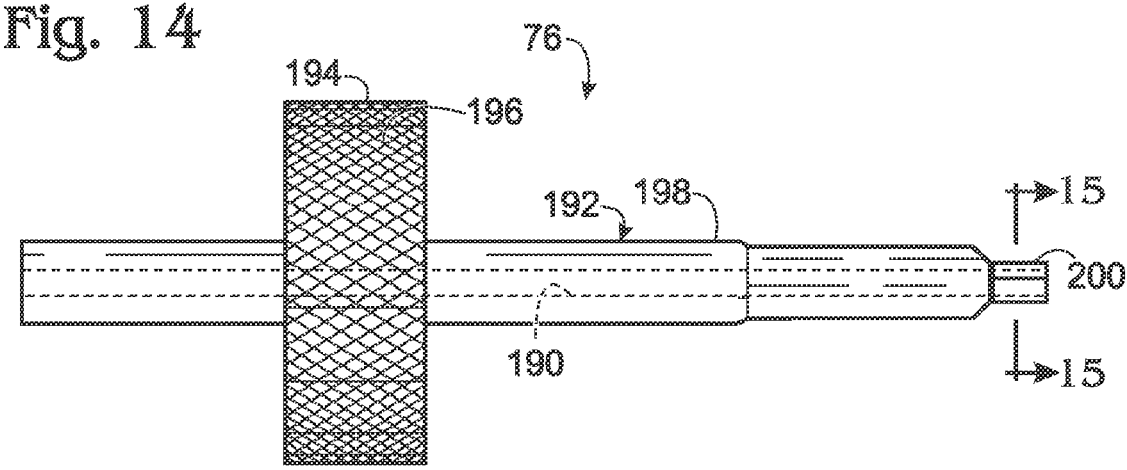
FIG. 14 is a side view of the driver of the system of FIG. 2, taken in isolation from other system components.
Figure 15:
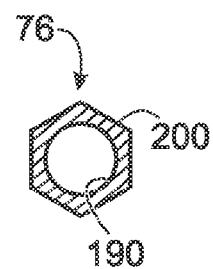
FIG. 15 is a cross-sectional view of the driver of FIG. 14, taken generally along line 15-15 of FIG. 14 through a fastener engagement structure formed at a distal end of the driver.

FIGS. 14 and 15 show driver 76 of system 50. The driver may be cannulated, with a longitudinal bore 190 extending through a shaft 192 thereof. A handle 194 may be attached to the shaft to enable manipulation (e.g., rotation) of the shaft. The handle may be arranged coaxially with the shaft and may have a knurled perimeter 196 to facilitate grasping the handle. The handle may be cylindrical (e.g., a disk).

Shaft 192 may have any suitable structure. The shaft may have a length that allows driver 76 and fastener 50 to be disposed on the wire of a guide at the same time, with the wire extending proximally from the driver and distally from the fastener (e.g., see FIG. 2). Shaft 192 may have a body 198 and a fastener engagement structure or tip 200 projecting distally from the body.

II. Methods of Installing a Flexible Fastener

The section describes exemplary methods of installing a flexible fastener in bone; see FIGS. 16-25. The steps presented in this section may be performed in any suitable order and in any suitable combination, and with any suitable combination of system components and component features of the present disclosure. Exemplary steps are illustrated with system 70 including fastener 50.

Figure 16:
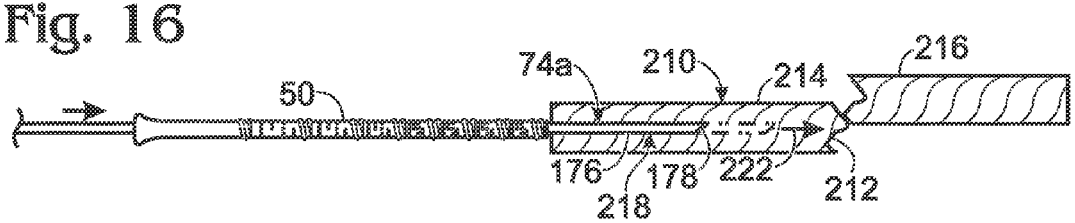
FIGS. 16-24 are a series of configurations produced with a fractured bone and the system of FIG. 2 during performance of an exemplary method of fixing bone and 20, in accordance with aspects of the present disclosure.

FIG. 16 schematically shows bone 210 into which the fastener will be introduced. The bone may be a single bone or two or more bones. Exemplary bone that may be suitable include at least one bone of the arms (humerus, radius, and/or ulna), wrists (carpal), hands (metacarpal and/or phalange), legs (femur, tibia, and/or fibula), feet (talus, calcaneus, tarsal, metatarsal, and/or phalange), ribs, spine, pelvis, or cranium, or a sternum, clavicle, mandible, scapula, or any combination of adjacent bones, among others. The bone may have at least one discontinuity 212, such as a fracture, a cut, or a joint region at which a pair of bones articulate. In the present illustration, discontinuity 212 is a fracture that divides a single bone into a pair of discrete portions 214, 216 (e.g. such as bone "pieces," interchangeably termed "segments"). In other examples, the bone portions may be provided by distinct bones separated by an anatomical joint. Bone portions 214 and 216 may be naturally offset from each other, may be offset as a result of injury, or may have no offset. In any event, use of a flexible fastener allows the surgeon to customize placement of the fastener according to the particular anatomy or condition encountered in a patient.

A first section or increment 218 of a path for fastener 50 may be defined by guide 74a, which has a linear distal end portion 176a. Alternatively, the first section of the path may be a nonlinear (e.g., curved) section defined by a guide having a nonlinear distal end portion. In any event, guide 74a may be driven into bone 210 by application of force to the guide, optionally before any part of fastener 50 has entered bone. For example, the surgeon may push on the guide's handle to urge the wire of the guide into bone, indicated by an arrow at 222, optionally while pivoting the handle slightly in a reciprocating motion to encourage travel of the wire. The depth and position of tip 178 in the bone may, for example, be monitored by fluoroscopy and/or by comparison of the position of one or more reference marks on the wire (e.g., see FIGS. 11 and 12) to the position of fastener 50 (if abutted with bone, as shown) and/or to a surface region of the bone. Fastener 50 may remain outside bone 210, and optionally may remain stationary, while distal end portion 176a of guide 74a is being driven into bone. In some cases, a pilot hole may be formed in the bone with another tool (such as a drill), before the distal end portion of guide 74a is driven into bone.

Figure 17:
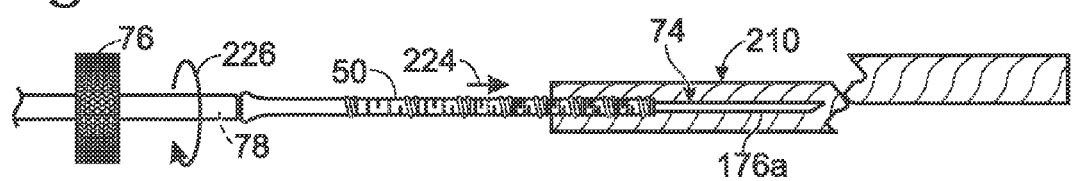

FIG. 17 shows fastener 50 being advanced into bone 210, indicated by an arrow at 224, by operation of driver 76, indicated by an arrow at 226. The fastener is being turned by the driver about an axis defined by wire 78 of guide 74. The fastener travels along and over at least part of distal end portion 176a, with the distal end portion projecting into bone distally from the leading end of the fastener.

Figure 18:
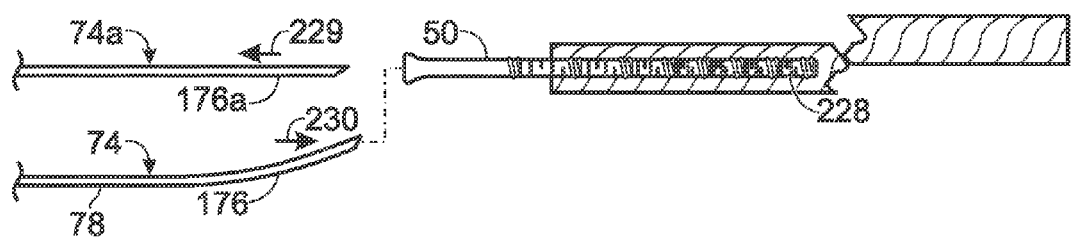

FIG. 18 shows guide 74a, with linear distal portion 176a, being replaced with guide 74, with curved distal end portion 176, after a leading end region 228 of fastener 50 has been advanced along a linear increment of the fastener's overall path into bone. Linear guide 74a has been removed from fastener 50, indicated by a motion arrow at 229. Curved guide 74 is about to be inserted into the fastener, indicated by a motion arrow at 230. Curved distal end portion 176 of guide 74 will be deformed to a linear configuration as wire 78 is being inserted into the distal region of the fastener, because the distal region is held in a linear configuration by surrounding bone. Guide 74 may be selected from a set of different guides (e.g., see FIG. 13) according to the desired path to be followed by the fastener.

Figure 19:
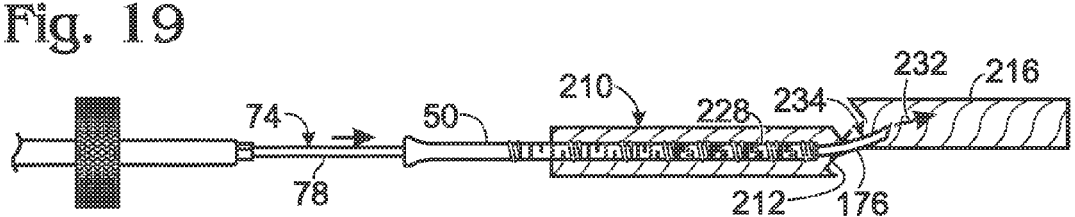

FIG. 19 shows guide 74 after the tip of wire 78 has been placed through fastener 50. Distal end portion 176 of the wire is being driven ahead of fastener 50, indicated by a motion arrow at 232, across fracture 212, and into distal bone portion 216. Distal end portion 176 of wire 78 creates a curved path 234 according to the preformed curvature of the distal end portion. In other words, the distal end portion of the wire may be held in a linear configuration within fastener 50, because the fastener is held in a linear configuration by the bone, and then projects nonlinearly from the fastener as distal end portion 176 is driven out of leading end region 228 of the fastener. Bone 210 and wire 78 may be visualized by fluoroscopy as the wire is being driven forward, to monitor the prospective trajectory of the fastener. Also, guide 74 may be wiggled pivotally to encourage travel of the wire into bone.

Figure 19A:
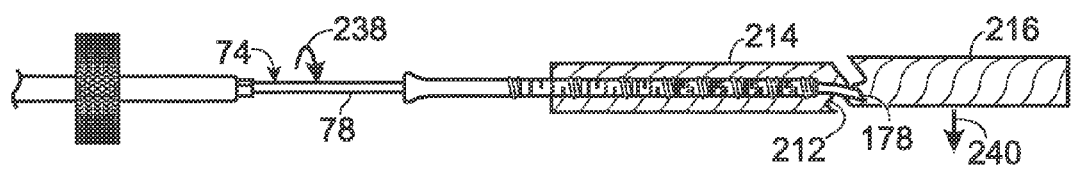

FIG. 19A shows an exemplary use of guide 74, as an alternative or supplement to the step illustrated in FIG. 19, to reduce the fracture and improve the alignment of bone portions 214, 216 during fastener 50 installation. Tip 178 of wire 78 may be advanced across discontinuity 212 and into distal bone portion 216. Guide 74 may be pivoted, indicated by a motion arrow at 238 to reposition distal bone portion 216 with respect to proximal bone portion 214, indicated by a motion arrow at 240.

Figure 20:
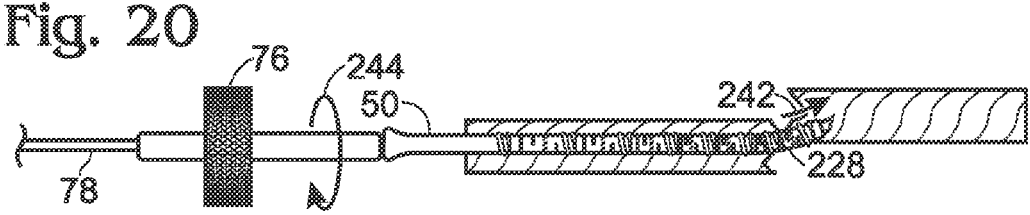

FIG. 20 shows a configuration following the configuration of FIG. 19 (rather than FIG. 19A). Leading end region 228 of fastener 50 is being advanced along a curved travel path, indicated by a motion arrow at 242, at least in part by rotation of driver 76, indicated by an arrow 244. The distal end portion of wire 78 acts as a track over and along which the end of the fastener travels. Accordingly, leading end region 228 of the fastener bends away from the linear travel path defined earlier by guide 74a (compare FIG. 20 with FIGS. 17 and 18).

Figure 21:
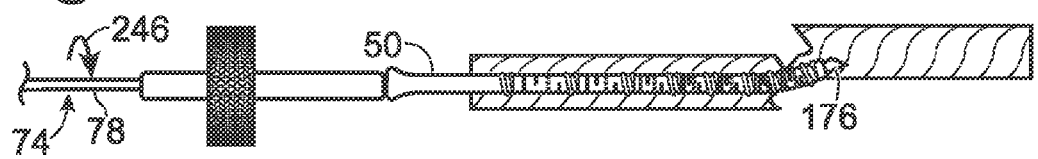

FIG. 21 shows pivotal reorientation of guide 74, indicated by a motion arrow at 246, to change the direction in which distal end portion 176 of wire 78 will be driven from the leading end of fastener 50. For example, here, guide 74 has been pivoted about one-half turn. Alternatively, guide 74 may be replaced with a different guide (e.g., see FIGS. 13 and 18) to guide a curved increment or a linear increment of the fastener's whole travel path.

Figure 22:
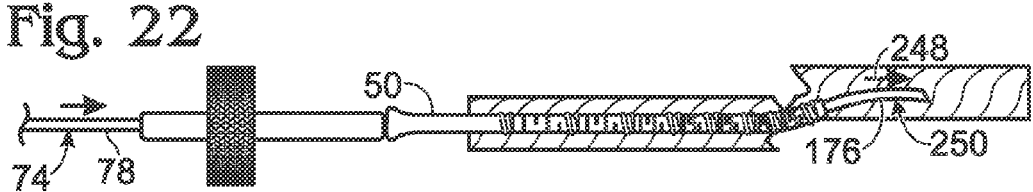

FIG. 22 shows wire 78 of guide 74 being driven ahead of fastener 50, indicated by an arrow at 248, generally as described for FIG. 19. Distal end portion 176 is being positioned to guide a third increment 250 of the fastener's whole travel path, with the third increment curving downward rather than upward as in FIG. 19.

Figure 23:
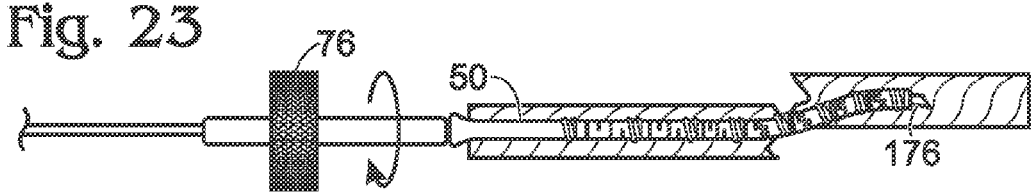

FIG. 23 shows fastener 50 after advancement along the third increment of the fastener's overall travel path, generally as described for FIG. 20, at least in part by rotation of driver 76.

Figure 24:
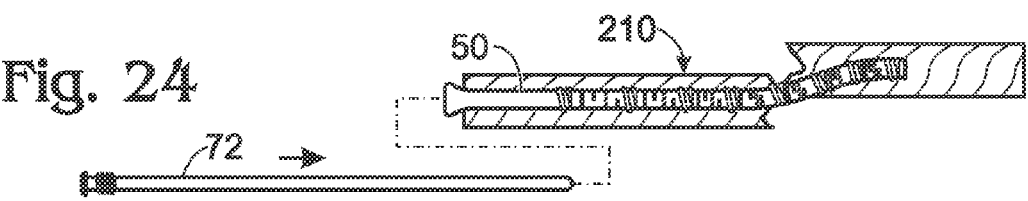

FIG. 24 shows fastener 50 at its final position in bone 210. Guide 74 has been removed and stiffener 72 is ready to be placed into the fastener to stiffen and reinforce the fastener. The stiffener may be attached to the fastener, such as with a threaded connection.

Figure 25:
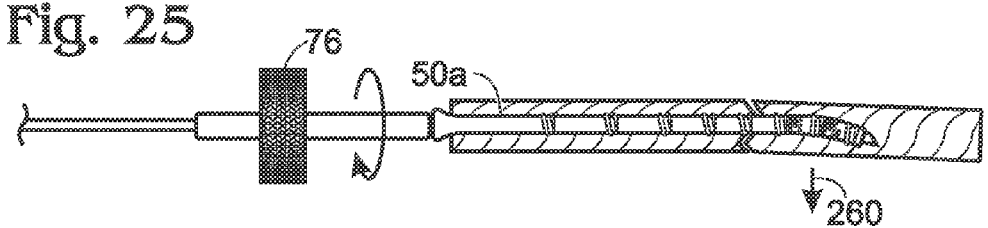
FIG. 25 is a configuration produced with the fractured bone of FIGS. 16-24, instruments of the system of FIG. 2, and an embodiment of a fastener that is flexible in a distal region of the fastener and less flexible in a proximal region of the fastener, and showing fracture reduction caused by spanning the fracture with the less flexible distal region of the fastener, in accordance with aspects of the present disclosure.

FIG. 25 shows a reduced configuration of the bone produced by a less flexible fastener embodiment (fastener 50a). In some cases, the fracture may be reduced by advancement of the fastener. The fastener may have a more flexible distal portion and a less flexible proximal portion. After the more flexible distal portion crosses the fracture, advancement of the more rigid proximal portion across the fracture, to span the fracture, can cause movement, indicated by an arrow at 260, of a distal bone portion relative to a proximal bone portion to improve alignment.

III. Rib Fixation with a Flexible Fastener

This section describes an exemplary flexible fastener for rib fixation and methods of implanting the fastener to fix a rib bone; see FIGS. 26-38. The fastener may be implanted with or without a stiffener (e.g., stiffener 72) and/or the use of a guide (e.g., guide 74) (see FIGS. 2 and 16-24).

Figure 26:
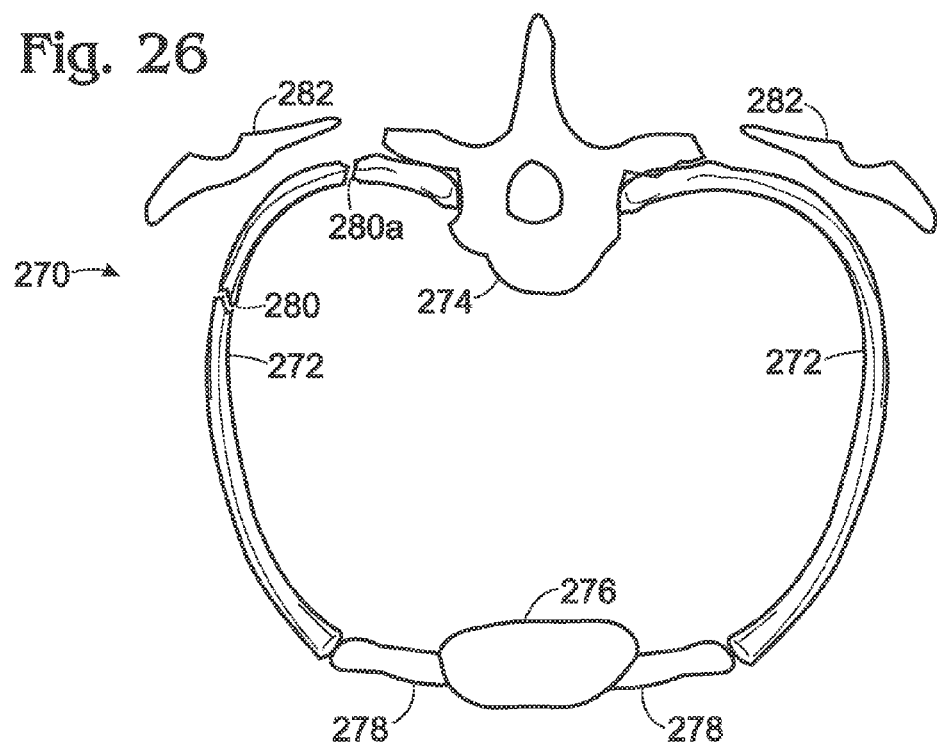
FIG. 26 is a somewhat schematic sectional taken through a fractured rib cage between ribs, in a direction transverse to the spine, and illustrating the curvature present in the ribs and potential impediments to installation of a fixation device to fix one or more of the depicted fractures, in accordance with aspects of the present disclosure.

FIG. 26 shows a transverse sectional view of a human rib cage 270. The rib cage, or thoracic cage, is composed of bone and cartilage that surround the chest cavity and organs therein, such as the heart and the lungs. In humans, the rib cage typically consists of 24 ribs 272, twelve thoracic vertebrae 274, a sternum 276 (or breastbone), and costal cartilages 278. The ribs, such as the pair of ribs 272 shown, articulate with thoracic vertebrae 274 posteriorly and, with the exception of the bottom two pairs of ribs (the floating ribs), are connected to sternum 276 anteriorly by costal cartilages 278.

Ribs can be fractured by trauma to the chest region and/or during surgery. Rib fractures often are particularly painful and difficult to treat, due to the hoop stress applied to the ribs during normal breathing. In many instances, single rib fractures are not actively treated, and limited motion is prescribed to give the fracture a chance to heal. However, in cases of severe or multiple fractures of the ribs, it may be desirable to stabilize the fractured bones mechanically. For example, when two or more fractures of the same rib occur, such as fractures 280 and 280a in FIG. 26, the result is one or more freely floating rib segments. This condition commonly is known as "flail chest."

A flail chest injury, multiple rib fracture of a similar nature, or a severe single rib fracture often must be stabilized to facilitate healing and to avoid further complications. Stabilization may be accomplished through the use of an implanted fixation device that attaches to the rib and that spans the fracture(s).

Bone screws can offer advantages over other fixation devices. The advantages can include stable engagement of bone, rapid installation, and less damage to the bone's periosteum. However, the curvature of ribs and positional interference from adjacent bones (e.g., a scapula 282 and/or a vertebra 274; see FIG. 26) make bone screws difficult to install effectively in ribs.

Figure 27:
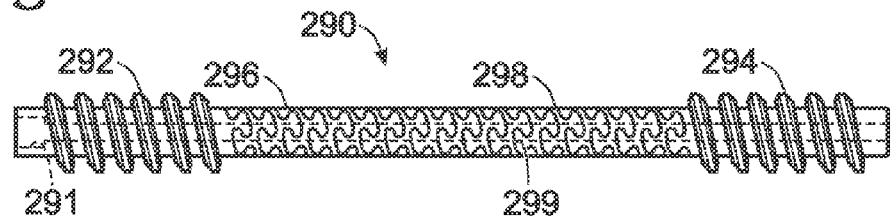
FIG. 27 is a side view of an exemplary flexible fastener for rib fixation, in accordance with aspects of the present disclosure.

The system disclosed herein can be utilized to place a flexible fastener along the medullary cavity of the rib. FIG. 27 shows an exemplary flexible fastener 290 that may be suitable. The fastener may be headless, as shown, or may include a proximal head. The use of a headless fastener can facilitate advancement of the proximal end of the fastener into the rib bone, such as to provide a substantially flush or recessed configuration of the fully-installed fastener with respect to the rib. The fastener may be cannulated: a longitudinal channel 291 may extend from one end to the other end of the fastener. The channel may widen near the trailing boundary of the fastener to provide a receiver for the tip of a driver.

Fastener 290 may have a proximal thread 292 and a distal thread 294 separated by a nonthreaded portion 296 of a shaft 298. The shaft may be flexible along any suitable portion of the fastener's length. For example, here, shaft 298 is rendered flexible by a helical slot 299 extending generally from one thread 292 to the other thread 294. Slot 299 may (or may not) be serpentine, as shown here. In other examples, the slot may extend into and/or through one or more threaded regions of the fastener.

Figure 28:
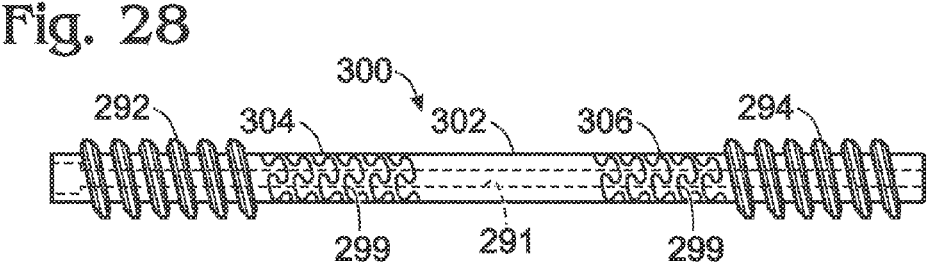
FIG. 28 is a side view of another exemplary flexible fastener for rib fixation, with the fastener having a pair of flexible regions separated by a rigid region of the fastener's shaft, in accordance with aspects of the present disclosure.

FIG. 28 shows another exemplary flexible fastener 300 for rib fixation. Fastener 300 is similar to fastener 290 except for the presence of a rigid region 302 of the shaft opposingly flanked by a pair of flexible regions 304, 306. Each flexible region 304 and 306 may be created by a discrete slot(s) 299. Rigid region 302 may be positioned, when the fastener is installed, to overlap a fracture or other discontinuity in a rib bone. Accordingly, the rigid region may span the discontinuity in the rib to provide more rigid fixation of the rib than fastener 290.

FIG. 29 shows a longitudinal sectional view of a fractured rib 272. Because the rib is thin, placement of a fastener transverse to the long axis of the rib can be problematic. The rib defines a curved medullary cavity 312 extending substantially the entire length of the rib. The cavity is surrounded by dense cortical bone 314 that is resistant to penetration by the fastener, particularly at an acute angle. Accordingly, the cortical bone can guide a flexible fastener along cavity 312.

FIGS. 29-32 show a series of fragmentary views of fractured rib 272 during performance of an exemplary method of fixing the rib with a flexible fastener 290 (shown schematically). In other examples, any other flexible fastener (e.g., fastener 50 of FIG. 2 or fastener 300 of FIG. 28, among others) may be utilized instead, with the fastener having any suitable combination of features of the present disclosure. The steps described here may be performed in any suitable order and combination.

FIG. 29 shows rib 272 prepared for fastener installation. An entry site 320 may be formed in a wall 322 of the rib to gain access to medullary cavity 312. For example, as shown here, the entry site may be formed on an outer side 324 of the rib, from outside the rib cage. The fastener may (or may not) be guided into the rib with a guide. For example, the leading region of a guide wire 326 may be placed into the rib and across fracture 310 before fastener installation. Alternatively, or in addition, the fastener may be guided into the rib with one or more guides (e.g., guides 74 and 74a-f; see FIG. 13 and FIGS. 16-24). In other words, the path to be followed by the fastener may be defined by the medullary cavity without a guide or with a single guide (e.g., a single guide wire 326), or defined incrementally with one or more wires including at least one wire having preformed longitudinal curvature (e.g., see FIGS. 16-24).

FIG. 30 shows fastener 290 positioned adjacent entry site 320 before entry into the rib. Entry site 320 may permit a distal portion 327 of the fastener to enter the rib obliquely to the local long axis of the rib, indicated by an arrow at 328.

FIG. 31 shows fastener 290 in a partially installed configuration. The fastener may be turned, indicated by an arrow at 330, to advance, indicated by an arrow at 332, the distal portion of the fastener along medullary cavity 312 and toward fracture 310.

FIG. 32 shows fastener 290 in a completely installed configuration. The distal portion of the fastener has been advanced across fracture 310 such that the fastener spans the fracture and both proximal and distal threaded regions 292, 294 are in threaded engagement with rib 272. Once installed, fastener 290 may extend along a nonlinear path that conforms at least in part to the longitudinal curvature of the rib.

FIGS. 33-36 show another series of fragmentary views of fractured rib 272 of FIG. 29 during performance of an exemplary method of fixing the rib with a flexible fastener, such as fastener 290. The steps described here may be performed in any suitable order and combination. An entry site 320 may be formed in a wall portion of the rib opposite that used in FIG. 29, to gain access to medullary cavity 312 (see FIG. 33 and compare with FIG. 29). More particularly, entry site 320 may be formed on an inner side 340 of rib 272, from inside the rib cage, and assisted by thoracoscopy. The entry site may permit the fastener to enter the rib obliquely to the local long axis of the rib (see FIG. 34). The fastener may be turned, indicated by an arrow at 330, to advance, indicated by an arrow at 332, the leading end region of the fastener along medullary cavity 312 and toward fracture 310 (see FIG. 35). The leading end region of the fastener may be advanced across fracture 310 such that the fastener spans the fracture, and both proximal and distal threaded regions 292, 294 are in threaded engagement with rib 272 (see FIG. 36). Once installed, the fastener may extend along a nonlinear path that conforms at least in part to the longitudinal curvature of the rib.

The path to be followed by the fastener may be defined by the medullary cavity, as shown here, without use of a guide. Alternatively, the path may be defined with a single guide (e.g., a single guide wire 326; see FIGS. 29-31), or defined incrementally with one or more wires including at least one wire having preformed longitudinal curvature (e.g., see FIGS. 16-24).

The fastener, at any stage, may be turned, indicated by an arrow at 348, with a flexible driver 350, such as an articulated driver. The driver may have a flexible shaft region 352 that allows proximal and distal portions of the driver's shaft to assume a range of angles relative to one another.

FIG. 37 shows another exemplary flexible fastener 370 for fixation of a bone, such as a rib bone. Fastener 370 has a proximal (trailing) screw element 372 and a distal (leading) screw element 374 each attached to a flexible member, such as a multi-strand cable 376. The cable may be fixed to a screw element at each of its opposing ends, such that the fastener can be turned as a unit. The cable may create a flexible region of the fastener, which may be opposingly flanked longitudinally by relatively more rigid screw elements 372, 374. The fastener may have a longitudinal passage 378 that extends through the fastener between its opposing ends. The passage is configured to receive a wire to guide the fastener along at least a portion of its overall travel path into bone. The wire may (e.g., see FIG. 13) or may not (e.g., see FIG. 29) have preformed longitudinal curvature. A single wire (e.g., see FIG. 29) or more than one wire (e.g., see FIGS. 16-24) may be used to guide the fastener into bone.

Each screw element 372, 374 may have at least one external thread 380, 382, respectively. The external threads may have the same pitch or different pitches, such as a greater pitch for a leading thread 382 relative to a trailing thread 380, as shown here, to apply longitudinal compression to the rib (or other bone).

FIG. 38 shows fractured rib 272 fixed with flexible fastener 370 and spanning a fracture 310 located in a posterior region of the rib. Fastener 370 may be placed into the rib via an entry site 320 formed in the outer side or the inner side of the rib, among others.

IV. Composition of System Components

Each system component (e.g., a fastener, wire, or stiffener) may have any suitable composition. Each may be formed of any suitable biocompatible material(s) and/or bioresorbable (bioabsorbable) material(s). Illustrative biocompatible materials that may be suitable for the fastener and/or stiffener of the fixation assembly include (1) metal (for example, titanium or titanium alloy, cobalt-chrome alloy, stainless steel, etc.); (2) polymer/plastic (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) bioresorbable material or polymer/plastic (for example, polymers of a-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.)); (4) bone material or bone-like material (e.g., bone chips, calcium phosphate crystals (e.g., hydroxyapatite, carbonated apatite, etc.)); or (5) any combination thereof.

The fastener and the stiffener may be formed of the same or different materials. For example, both may be formed of metal, both may be formed of polymer (e.g., plastic), both may be bioresorbable, the fastener may be formed of metal and the stiffener of polymer (which may be bioresorbable) (or vice versa), or the like. A wire may be formed of metal or polymer, among others.

V. Systems/Kits

The components disclosed herein may be combined in any suitable manner to provide a system, which may be supplied as a kit. The system (or kit) may include one or more fasteners and/or one or more stiffeners. The system also or alternatively may include any combination of the following: one or more guides (e.g., a set of two or more of the guides of FIG. 13), one or more drivers, at least one drill, and the like. Each system component may be configured for single use (e.g., fasteners and stiffeners) or for multiple use (e.g., the associated installation instruments). Some or all of the components of the system (or kit) may be provided in a sterile condition, such as packaged in a sterile container. The system (or kit) may be provided with instructions for fastener installation.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of bone fixation, the method comprising:
   moving a wire longitudinally, while the wire extends through a flexible fastener having a leading end in bone, such that a distal end portion of the wire having a preformed longitudinal curvature penetrates the bone ahead of the leading end of the fastener to create a curved path in the bone; and
   advancing the leading end of the fastener along at least a portion of the curved path with the leading end of the fastener guided by the distal end portion of the wire;
   wherein the steps of moving and advancing also are performed with a different wire such that the leading end of the fastener is advanced along at least a portion of a path created by a distal end portion of the different wire.

2. The method of claim 1, further comprising a step of placing the leading end of the fastener into the bone on a linear path before the steps of moving and advancing.

3. The method of claim 1, wherein the distal end portion of the different wire is linear.

4. The method of claim 1, wherein the distal end portion of the different wire is curved longitudinally.

5. The method of claim 1, further comprising a step of pivoting the wire about its long axis after the step of advancing and while the wire is extending into the fastener, to change a pivotal orientation of the distal end portion of the wire.

6. The method of claim 5, further comprising a step of repeating the steps of moving and advancing with the distal end portion of the wire generally in the changed pivotal orientation.

7. The method of claim 5, wherein the step of pivoting the wire is performed while the wire extends out of the fastener at the leading end, to adjust a position of a first bone portion and a second bone portion relative to one another.

8. The method of claim 1, wherein the step of moving includes a step of applying a driving force to the wire via a handle that indicates a direction of the preformed longitudinal curvature of the distal end portion of the wire.

9. The method of claim 1, further comprising a step of inserting an elongate insert into the fastener after the steps of moving and advancing, wherein the insert remains in the fastener while the bone heals.

10. A method of bone fixation, the method comprising:
    placing a leading end of a fastener into a first portion of bone;
    moving a wire longitudinally, while the wire extends through the fastener, such that a distal end portion of the wire contacts a second portion of bone ahead of the leading end of the fastener;
    pivoting the wire to change a position of the first portion and the second portion relative to each other; and
    advancing a leading end of the fastener into the second portion of bone.

11. A method of bone fixation, the method comprising:
    moving a wire longitudinally, while the wire extends through a flexible fastener having a leading end in bone, such that a distal end portion of the wire having a preformed longitudinal curvature penetrates the bone ahead of the leading end of the fastener to create a curved path in the bone;
    advancing the leading end of the fastener along at least a portion of the curved path with the leading end of the fastener guided by the distal end portion of the wire; and
    pivoting the wire about its long axis after the step of advancing and while the wire is extending into the fastener, to change a pivotal orientation of the distal end portion of the wire.

12. The method of claim 11, further comprising a step of placing the leading end of the fastener into the bone on a linear path before the steps of moving and advancing.

13. The method of claim 11, further comprising a step of repeating the steps of moving and advancing with the distal end portion of the wire generally in the changed pivotal orientation.

14. The method of claim 11, wherein the step of pivoting the wire is performed while the wire extends out of the fastener at the leading end, to adjust a position of a first bone portion and a second bone portion relative to one another.

15. The method of claim 14, further comprising a step of moving the wire longitudinally, while the wire extends through the fastener, such that a distal end portion of the wire contacts the second bone portion ahead of the leading end of the fastener.

16. The method of claim 11, wherein the step of moving includes a step of applying a driving force to the wire via a handle that indicates a direction of the preformed longitudinal curvature of the distal end portion of the wire.

17. The method of claim 11, further comprising a step of inserting an elongate insert into the fastener after the steps of moving and advancing, wherein the insert remains in the fastener while the bone heals.

18. A method of bone fixation, the method comprising:
    moving a wire longitudinally, while the wire extends through a flexible fastener having a leading end in bone, such that a distal end portion of the wire having a preformed longitudinal curvature penetrates the bone ahead of the leading end of the fastener to create a curved path in the bone, wherein the step of moving includes a step of applying a driving force to the wire via a handle that indicates a direction of the preformed longitudinal curvature of the distal end portion of the wire; and
    advancing the leading end of the fastener along at least a portion of the curved path, with the leading end of the fastener guided by the distal end portion of the wire.

19. The method of claim 18, further comprising a step of placing the leading end of the fastener into the bone on a linear path before the steps of moving and advancing.

20. The method of claim 18, further comprising a step of inserting an elongate insert into the fastener after the steps of moving and advancing, wherein the insert remains in the fastener while the bone heals.

* * * * *